(12) United States Patent
Boucher et al.

(10) Patent No.: US 11,576,803 B2
(45) Date of Patent: Feb. 14, 2023

(54) KNEE BRACE AND SYSTEM FOR CUSTOM FABRICATING KNEE BRACE FOR A USER

(71) Applicant: LABORATOIRE VICTHOM INC., Laval (CA)

(72) Inventors: Sylvain Boucher, Laval (CA); Louis Desrosiers, Laval (CA)

(73) Assignee: LABORATOIRE VICTHOM INC., Laval (CA)

( * ) Notice: Subject to any disclaimer, the term of this patent is extended or adjusted under 35 U.S.C. 154(b) by 876 days.

(21) Appl. No.: 16/461,903

(22) PCT Filed: Nov. 20, 2017

(86) PCT No.: PCT/CA2017/051383
§ 371 (c)(1),
(2) Date: May 17, 2019

(87) PCT Pub. No.: WO2018/090146
PCT Pub. Date: May 24, 2018

(65) Prior Publication Data
US 2019/0274859 A1    Sep. 12, 2019

Related U.S. Application Data

(60) Provisional application No. 62/424,015, filed on Nov. 18, 2016.

(51) Int. Cl.
*A61F 5/01*      (2006.01)
*G16H 50/50*   (2018.01)
*G16H 20/30*   (2018.01)

(52) U.S. Cl.
CPC ........... *A61F 5/0125* (2013.01); *G16H 50/50* (2018.01); *A61F 2005/0148* (2013.01); *A61F 2005/0151* (2013.01); *G16H 20/30* (2018.01)

(58) Field of Classification Search
CPC ........... A61F 5/0125; A61F 2005/0148; A61F 2005/0151; G16H 50/50; G16H 20/30
See application file for complete search history.

(56) References Cited

U.S. PATENT DOCUMENTS

| | | |
|---|---|---|
| 6,746,414 B1 | 6/2004 | Devreese |
| 2001/0056012 A1 | 12/2001 | Pellis |

(Continued)

FOREIGN PATENT DOCUMENTS

| | | | | |
|---|---|---|---|---|
| CN | 102695478 A | * | 9/2012 | ........... A61F 2/5046 |
| CN | 111281738 A | * | 6/2020 | |
| CN | 111383763 A | * | 7/2020 | |

*Primary Examiner* — Tarla R Patel
(74) *Attorney, Agent, or Firm* — Norton Rose Fulbright Canada LLP (57) ABSTRACT

A knee brace comprises a medial hinge device and a lateral hinge device each including an upper arm configured to be attached to a thigh, and a lower arm configured to be attached to a shank. An assembly joins free ends of the upper arm and of the lower arm in each of the medial hinge device and the lateral hinge device, the assembly of each of the medial hinge device and the lateral hinge device including an operative set of pivot and pivot slot, and another operative set of follower and at least one follower slot. The assemblies of the medial hinge device and a lateral hinge are configured to induce a corrective constraint on leg movement. A system for generating a knee brace customized to a patient is also provided.

18 Claims, 6 Drawing Sheets

(56) References Cited

U.S. PATENT DOCUMENTS

| | | | |
|---|---|---|---|
| 2005/0192522 A1 | 9/2005 | Houser | |
| 2009/0093891 A1* | 4/2009 | Summit | A61F 2/5046 602/3 |
| 2009/0182254 A1 | 7/2009 | Cho | |
| 2013/0226533 A1* | 8/2013 | Summit | B33Y 50/00 703/1 |
| 2015/0290010 A1 | 10/2015 | Nace | |
| 2020/0129237 A1* | 4/2020 | Ay | G16H 70/60 |

* cited by examiner

KNEE BRACE AND SYSTEM FOR CUSTOM FABRICATING KNEE BRACE FOR A USER

CROSS-REFERENCE TO RELATED APPLICATION

The present application claims the priority of U.S. Provisional Patent Application No. 62/424,15, filed on Nov. 18, 2016, the contents of which are incorporated herein by reference.

TECHNICAL FIELD

The application relates generally to a knee brace and, more particularly, to a knee brace effecting a corrective constraint in the knee movement of the user, and to a system for fabricating such knee braces.

BACKGROUND OF THE ART

Knee braces are conventionally used for different purposes. One of the known uses of knee braces is for correcting the knee movement. Indeed, the knee joint is a complex articulation in which the movement is guided by different anatomic features, such as the contact between articular condylar and/or bony surfaces of the femur, tibia and patella, the tension imposed by the ligaments articulating the bones. In fact, soft tissue laxity may cause some instability in the knee, which in turn may hamper the gait of a person, induce pain, and/or cause injury.

Various corrective knee braces are available. The hinges of such knee braces, which impose corrective constraints to the knee movement, may employ gears, racks, etc. Such hinges may be voluminous, and are hardly scalable to users of different heights. Also, knee braces may not induce a natural movement of the leg. Accordingly, many knee braces of the prior art come in a one-size fits all, or in a limited distribution of sizes. There may also be limits in the corrective effect of such knee braces for taller users or these with specific biomechanics, due to the limit in size of gears. There exists room for improvement in the customization of knee braces or components thereof.

SUMMARY

It is an aim of the present disclosure to provide a knee brace that addresses issues related to the prior art.

It is a further aim of the present disclosure to provide a system for generating a knee brace customized to a patient.

In accordance with a first embodiment of the present disclosure, there is provided a knee brace comprising: a medial hinge device and a lateral hinge device each including an upper arm configured to be attached to a thigh, a lower arm configured to be attached to a shank, and an assembly joining free ends of the upper arm and of the lower arm in each of the medial hinge device and the lateral hinge device, the assembly of each of the medial hinge device and the lateral hinge device including an operative set of pivot and pivot slot, and another operative set of follower and at least one follower slot; wherein the assemblies of the medial hinge device and a lateral hinge are configured to induce a corrective constraint on leg movement.

Further in accordance with the first embodiment, the assembly of the medial hinge device for instance has the pivot slot in its lower arm, and the assembly of the lateral hinge device has the pivot slot in its upper arm.

Still further in accordance with the first embodiment, the assembly of the medial hinge device has for instance the follower on its lower arm.

Still further in accordance with the first embodiment, the assembly of the lateral hinge device has for instance the follower on its upper arm.

Still further in accordance with the first embodiment, a cuff on the lower arm is for instance configured for receiving the shank.

Still further in accordance with the first embodiment, a cuff on the upper arm is for instance configured for receiving the thigh.

Still further in accordance with the first embodiment, the assemblies each include for instance a pair of spaced apart plates having the at least one follower slot and supporting the pivot, the upper arm being between the plates in the lateral hinge device, the lower arm being between the plates in the medial hinge device.

Still further in accordance with the first embodiment, each pair of the spaced apart plates has for instance a pair of the follower slots, with the follower extending into the pair of the follower slots in each pair of the spaced apart plates.

Still further in accordance with the first embodiment, the pivot slot of the assembly of the medial hinge device is for instance transversely oriented relative to the pivot slot of the assembly of the lateral hinge device when the knee brace is in flexion.

Still further in accordance with the first embodiment, the follower slots for instance have a chicane-like disruption.

Still further in accordance with the first embodiment, the follower slots are for instance custom-machined as a function of the corrective constraint specific to a user of the knee brace.

Still further in accordance with the first embodiment, the assemblies are for instance dimensioned as a function of the corrective constraint specific to a user of the knee brace.

In accordance with a second embodiment of the present disclosure, there is provided a system for generating a knee brace customized to a patient, comprising: a processing unit; and a non-transitory computer-readable memory communicatively coupled to the processing unit and comprising computer-readable program instructions executable by the processing unit for: receiving user data including at least a lengthening value and a rotation value for the knee joint of the user, the user data being indicative of a corrective constraint to leg movement specific to the user; determining dimensional parameters of a medial hinge device and of a lateral hinge device as a function of the user data; and generating a fabrication file for fabricating components of the medial hinge device and of the lateral hinge device with the determined dimensional parameters.

Further in accordance with the second embodiment, the fabrication file is for instance output.

Still further in accordance with the second embodiment, fabricating the components of the medial hinge device and of the lateral hinge device includes for instance using the fabrication file.

Still further in accordance with the second embodiment, fabricating the components comprises for instance driving fabrication equipment to fabricate the components.

Still further in accordance with the second embodiment, determining the dimensional parameters includes for instance determining a size and a shape of follower slots in each of the medial hinge device and of the lateral hinge device.

Still further in accordance with the second embodiment, a position and orientation of the follower slots relative to one another is for instance determined.

Still further in accordance with the second embodiment, determining the dimensional parameters includes for instance determining a position and orientation of set of pivot and pivot slot in both the medial hinge device and lateral hinge device.

Still further in accordance with the second embodiment, determining the dimensional parameters includes for instance simulating movement of a virtual model of a knee brace to obtain the lengthening value and a rotation value.

DESCRIPTION OF THE DRAWINGS

Reference is now made to the accompanying figures in which.

DETAILED DESCRIPTION

Figure 1:
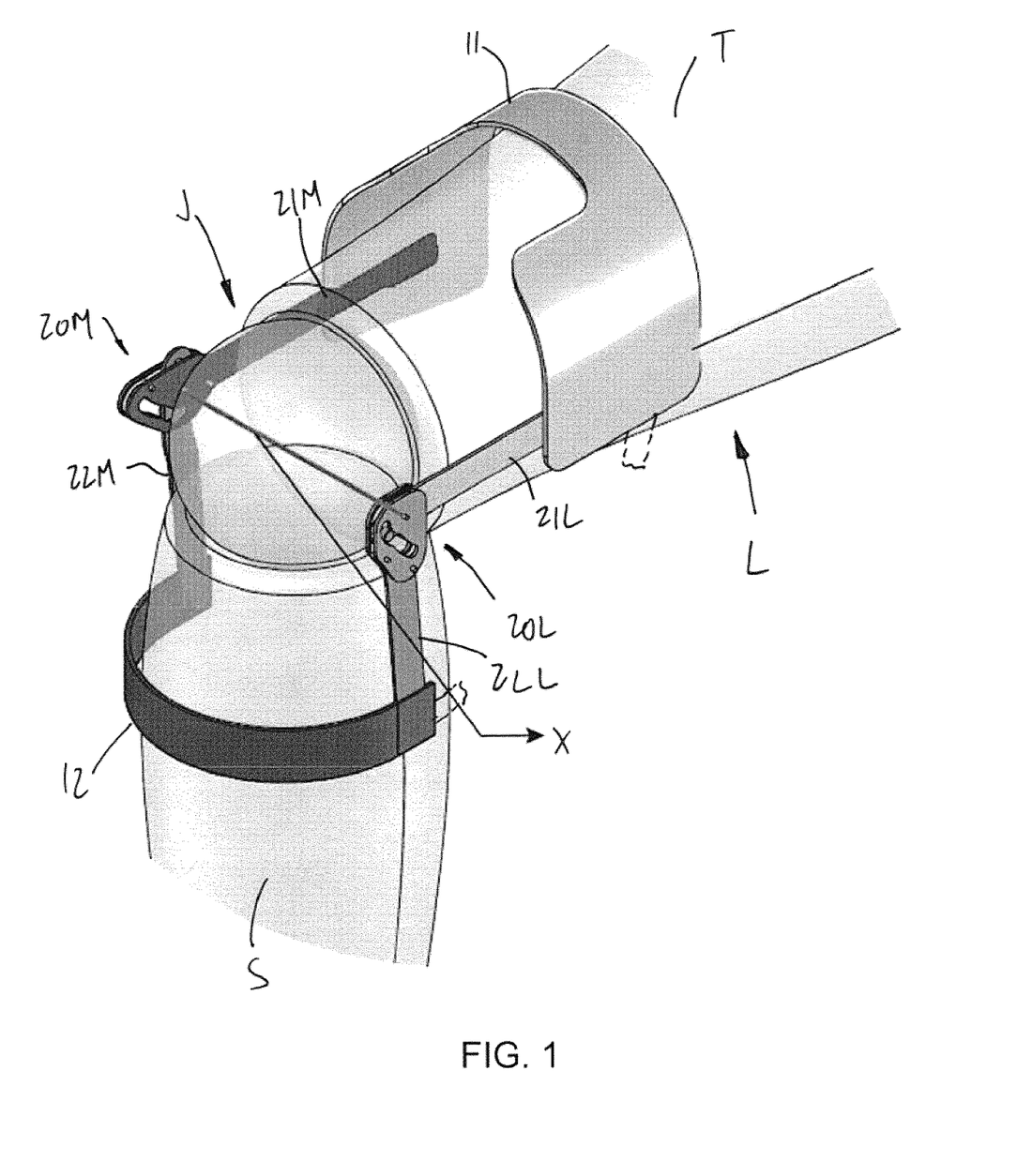
FIG. 1 is a perspective view of a knee brace in accordance with the present disclosure, as mounted to a user leg.

Referring to the drawings and more particularly to FIG. 1, a knee brace in accordance with the present disclosure is generally shown at 10. The knee brace 10 may also be known as knee orthosis, knee support, but reference is made herein to knee brace for consistency. The knee brace 10 is of the type imposing a corrective constraint in the movement of the knee, i.e., the reciprocating movement between flexion and extension, for instance during a walking or running action of the user. The knee brace 10 may also be said to modify the functional and/or structural characteristics of the knee joint. Therefore, the knee brace 10 is non-invasively secured to the leg L of the user in the manner shown in FIG. 1. The leg L has a shank S and a thigh T, interrelated at the knee joint J. It bears mentioning that the knee joint J typically allows rotation(s) and translation(s) of the shank S relative to the thigh T.

Still referring to FIG. 1, the knee brace 10 has a thigh cuff 11 and a shank cuff 12. The cuffs 11 and 12 are shown schematically for simplicity, but have appropriate fastening means to be secured to the thigh T and shank S, respectively, in such a way that there is limited or no movement between the cuff 11 and the tight T, and between the cuff 12 and the shank S, once the cuffs 11 and 12 are secured to the leg L. For example, the fastening means may include straps, belts, with Velcro™, eyelets, etc, to fasten the cuffs 11 and 12 to the leg L. Moreover, the cuffs 11 and 12 may have rigid structural components such as those shown in FIG. 1, to which the straps, belts, or like fastening means may be connected. The rigid structural components are shown as arches, and may have other components, such as padding, cushioning, etc, for the cuffs 11 to 12 to be ergonomically applied against the leg L, whether it be directly against the skin or over garment.

The cuffs 11 and 12 are interrelated by a pair of hinge devices 20. The hinge devices 20 are shown in greater detail in FIG. 2. The hinge devices 20 and their components are concurrently referred to in the description without letters affixed to them, but may also be referred to in the description and depicted in the figures with a "L" for "lateral" or a "M" for "medial", as a function of their anatomical location, i.e., laterally or medially in the knee joint J. The hinge devices 20L and 20M may have the same components, but their arrangements differs, as detailed below. However, for simplicity and efficiency of the text, concurrent reference of the hinge devices 20 is made herein.

Figure 2:
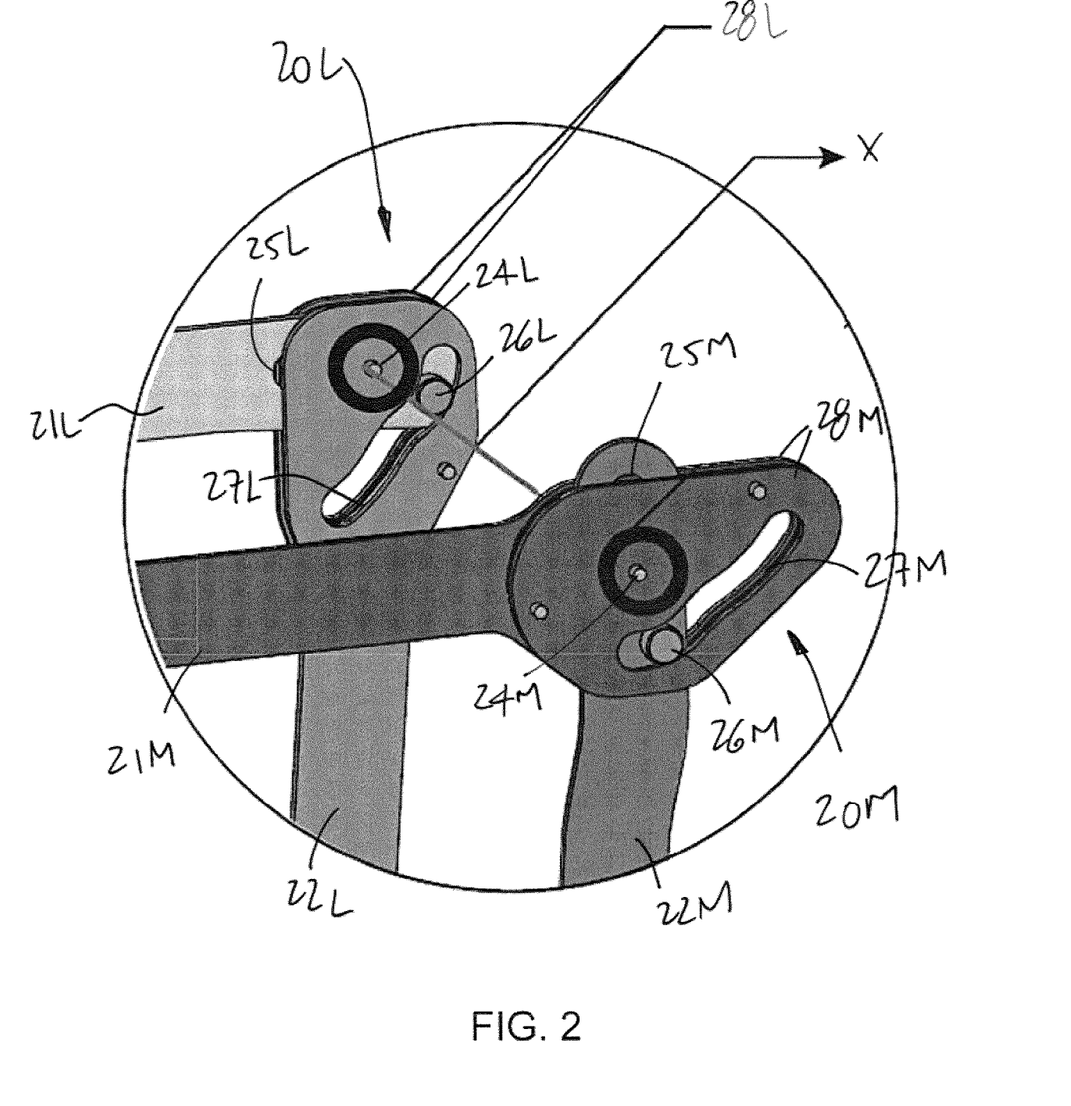
FIG. 2 is an enlarged fragmented view of the knee brace of FIG. 1, showing medial and lateral hinge devices thereof.

Each of hinge devices 20 has an upper arm 21 and a lower arm 22. The upper arm 21 has its top end connected to the cuff 11, whereas the lower arm 22 has its bottom end connected to the cuff 12. In an embodiment, the connection between arms 21 and cuff 11, and between arms 22 and cuff 12, is a rigid fixed connection. The upper arms 21 and the lower arms 22 of each of the hinge devices 20 meet and are operatively connected at the joint portion of the hinge devices 20. In each hinge device 20, the connection between the upper arm 21 and the lower arm 22 has an assembly that may include a pivot 24 paired with a pivot slot 25, and a follower 26 paired with a follower slot(s) 27. According to an embodiment, each of the hinge devices 20 has a plate 28 or a pair of spaced apart plates 28, supporting the pivot 24 and defining the follower slots 27. The expression slot 27 is used, but other expressions include channel or groove. The slots may or may not extend through the arms 21 and 22 and plates 28, i.e., from a face to another of the arms 21 and 22 and plates 28.

Still referring to FIG. 2, in the medial hinge device 20M, the plates 28M are at an end of the upper arm 21M and define a gap therebetween. The plates 28M may be releasably attached (e.g., with fasteners) or permanently fixed to the upper arm 21M (e.g., welding, monolithic construction, etc). The pivot 24M has its ends connected to the plates 28M such that the pivot 24M extends through the gap, transversely to planes of the plates 28M. The pivot 24M passes through the pivot slot 25M defined in the lower arm 22M, whereby the pair of pivot 24M and pivot slot 25M provides at least two degrees of freedom (DOF), including a rotation about the pivot 24M and a translation of the pivot 24M in the pivot slot 25M. According to an embodiment, the pivot slot 25M has an elongated oblong or rectangular shape, for movement of the pivot 24M along a straight path in the pivot slot 25M.

Still in the medial hinge device 20M, each of the plates 28M has a follower slot 27M, with the two follower slots 27M mirroring each other. The follower slots 27M extend from side to side of the plates 28M, although the follower slots 27M may also be in a single surface of the plates 28M, i.e., the surface facing the gap. Moreover, it is considered to provide a follower slot 27M in a single one of the plates 28M, for instance if the medial hinge device 20M has a single plate 28M. The follower 26M projects from both sides of the lower arm 22M and penetrates the follower slots 27M, for guided movement of the follower 26M along the follower slots 27M. If a single one of the plates 28M has a follower slot 27M, then the follower 26M would project from a single side of the lower arm 22M. The followers 26 may be common circular pins. The followers 26 may also include a bearing to support the circular pins or may have bearings received in the follower slots 27M.

As a result of the assembly described above for the medial hinge device 20M, the pairs of pivot 24M and pivot slot 25M, and of follower 26M with follower slot(s) 27M impose a movement constraint of the upper arm 21M relative to the lower arm 22M, the movement constraint resulting in a combination of rotation and translation of the upper arm 21M relative to the lower arm 22M. The magnitude of the rotation and translation of the upper arm 21M relative to the lower arm 22M is based on the dimensions and shapes of the pivot slot 25M and the follower slot(s) 27M.

Still referring to FIG. 2, in the lateral hinge device 20L, the plates 28L are at an end of the lower arm 22L and define a gap therebetween. The plates 28L may be releasably attached (e.g., with fasteners) or permanently fixed to the lower arm 21L (e.g., welding, monolithic construction, etc). The pivot 24L has its ends connected to the plates 28L such that the pivot 24L extends through the gap transversely to planes of the plates 28L. The pivot 24L passes through the pivot slot 25L defined in the upper arm 21L, whereby the pair of pivot 24L and pivot slot 25L provides at least two degrees of freedom (DOF), including a rotation about the pivot 24L and a translation of the pivot 24L in the pivot slot 25L. According to an embodiment, the pivot slot 25L has an elongated oblong or rectangular shape, for movement of the pivot 24L along a straight path in the pivot slot 25L.

Still in the lateral hinge device 20L, each of the plates 28L has a follower slot 27L, with the two follower slots 27L mirroring each other. The follower slots 27L extend from side to side of the plates 28L, although the follower slots 27L may also be in a single surface of the plates 28L, i.e., the surface facing the gap. Moreover, it is considered to provide a follower slot 27L in a single one of the plates 28L, for instance if there is only one of the plates 28L in the lateral hinge device 20L. The follower 26L projects from both sides of the upper arm 21L and penetrates the follower slots 27L, for guided movement of the follower 26L along the follower slots 27L. If a single one of the plates 28L has a follower slot 27L, then the follower 26L would project from a single side of the lower arm 22L. The follower 26L may have a similar configuration as the follower 26M, with bearing(s). In fact, any follower or pivot may employ bearings.

As a result of the assembly described above for the lateral hinge device 20L, the pairs of pivot 24L and pivot slot 25L, and of follower 26L with follower slot(s) 27(L) impose a movement constraint of the upper arm 21L relative to the lower arm 22L, the movement constraint resulting in a combination of rotation and translation of the upper arm 21L relative to the lower arm 22L. The magnitude of the rotation and translation of the upper arm 21L relative to the lower arm 22L is based on the dimensions and shapes of the pivot slot 25L and the follower slot(s) 27L. Due to the arrangement of components between the medial hinge device 20M and the lateral hinge device 20L, there will result a corrective constraint on the leg of the person wearing the knee brace 10, by the cumulative effect of the constraint imposed by the lateral hinge device 20L and the medial hinge device 20M. In particular, the transverse relation (i.e., orientation) between the pivot slots 25M and 25L is responsible for inducing a constraint as described in further detail hereinafter and shown in FIGS. 4 and 5. Contrary to the illustrated embodiment, the lateral hinge device 20L and the medial hinge device 20M may be similar to one another in having the plates 28 on the same arms (i.e., both upper arms 21, or both lower arms 22), and hence having the pivots 24 on the same opposed arms.

In order to explain the corrective constraint induced on the leg L, the knee brace 10 is shown having an articular axis X, essentially representing the articular center of the knee joint J. The axis X is defined as passing through the pivots 24 of the knee brace 20. As explained hereinafter, during the flexion-extension movement, the axis X is not fixed in space.

Figure 3:
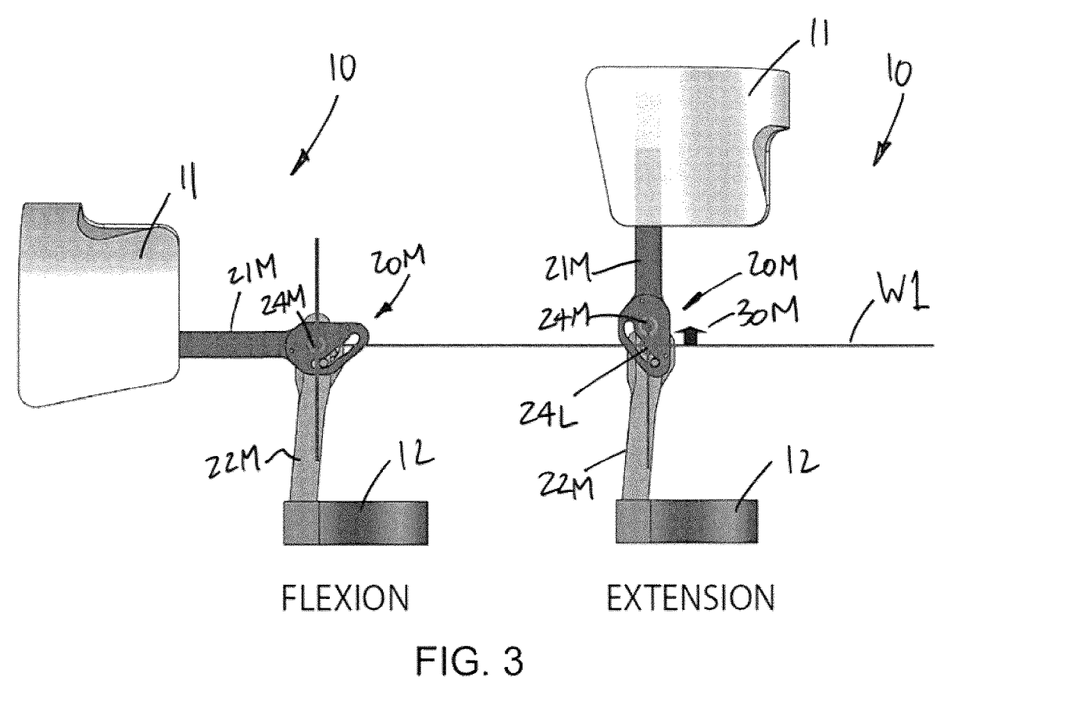
FIG. 3 is a medial elevation view of the knee brace of FIG. 1, in flexion and extension.

Referring to FIG. 3, the hinge device 20M is shown, and is in flexion in the left-hand side and in extension in the right-hand side. The line shown as W1 in FIG. 3, extending to both the extension and the flexion views, is representative of a virtual plane in which lie the axis X of the knee brace 10 in flexion, and the pivot 24L in extension. Therefore, the hinge device 20M is constrained in the knee brace 10 to have its pivot 24M move upwardly, from flexion to extension, relative to the pivot 24L. In other words, the pivot 24M moves upwardly in the frontal plane of the user. This may result in a lengthening of the leg of the patient when the leg is extended, by using the elasticity of the soft tissue, and tensioning same. However, the hinge devices 20 may concurrently act so as not to provide any such leg extension.

Figure 4:
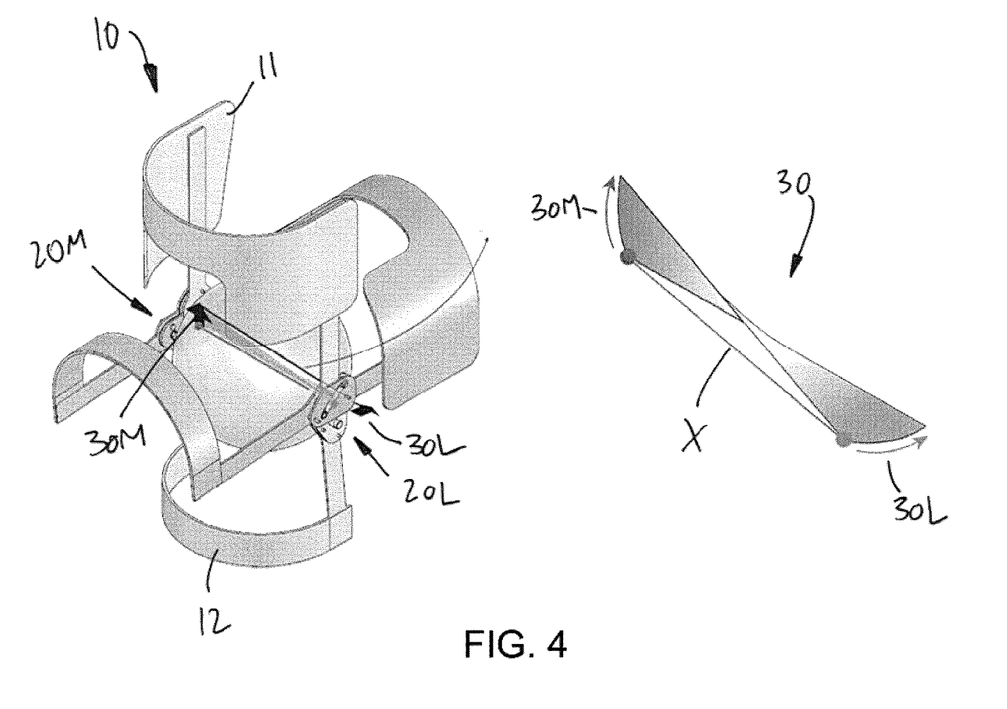
FIG. 4 is a perspective view of the knee brace of FIG. 1, showing a corrective constraint from the flexion to extension.
Figure 5:
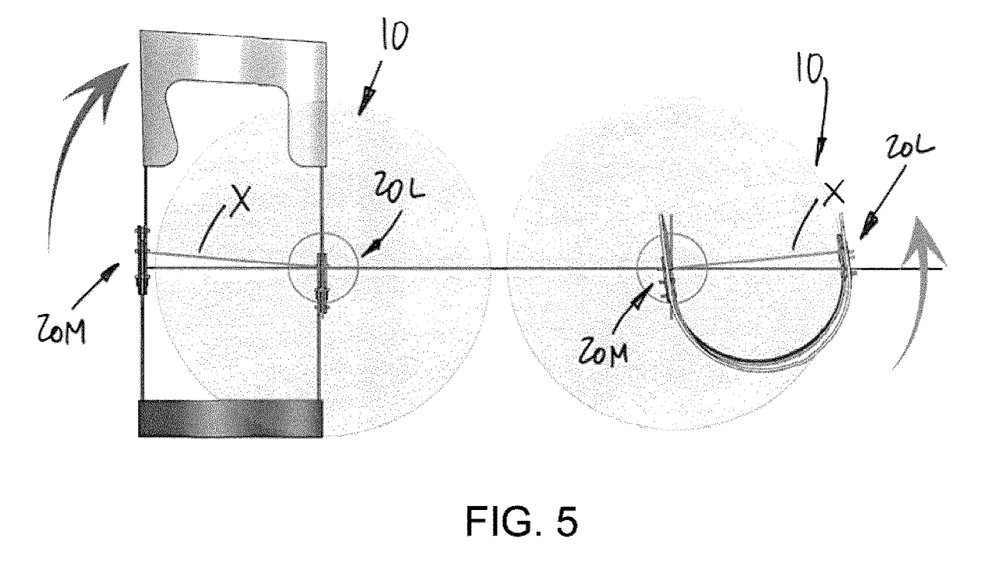
FIG. 5 shows corrective constraint in the frontal plane and in the transverse plane of the knee brace.

Referring to FIG. 4, the movements shown in a two-dimensional manner in FIG. 3 are shown in a three-dimension manner, as illustrated at 30. The arrows 30M and 30L are indicative of the concurrent medial upward movement 30M and the lateral rearward 30L movement constraints imposed by the knee brace 10. Accordingly, the movements 30M and 30L include medial and lateral end points for the pivot axis X, in leg extension and in leg flexion, and a distance between the lateral end points, and between the medial end points. Again, the magnitude of the movements 30M and 30L may be determined by the size of the pivot slots 25 and the follower slots 27, as a function of desired leg lengthening and rotation to correct knee movement. As shown in FIG. 5, the movements may not be purely vertical or horizontal, but rather movements along an arc of a circle relative to the opposite pivot 24. However, as a ratio of radius to arc is substantially greater than 1:1, the movements are quasi vertical or quasi horizontal.

Figure 6:
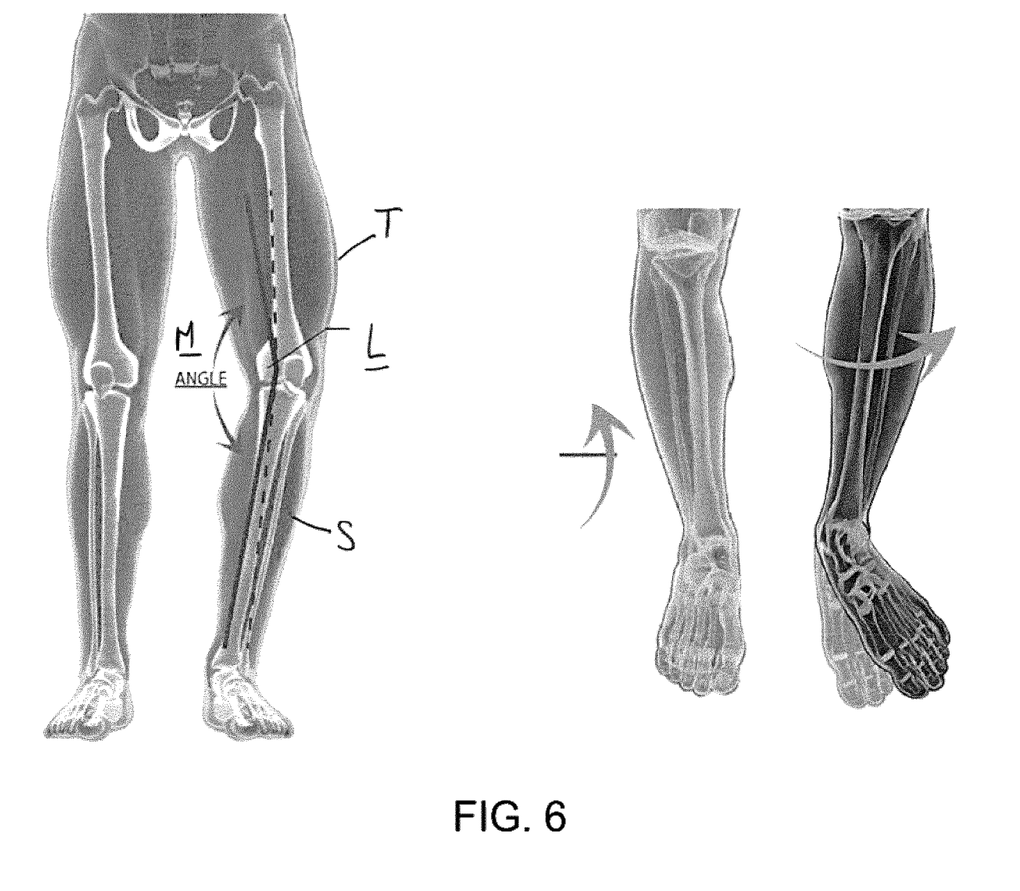
FIG. 6 shows an impact of the corrective constraint of the knee brace on the leg.

Referring to FIG. 6, the impact on the leg is shown. The medial upward movement may increase the angle between the mechanical axis of the tibia and the mechanical axis of the femur, as shown on the right-hand side. This may be caused by a lengthening of the leg (also known as distraction) as a result of the action of the knee brace 10 when the leg is moved into extension. Likewise, the lateral rearward movement may cause an external rotation of the foot. Internal rotation of the foot may also be induced with a rearrangement of the components of the hinge devices 20M and 20L.

As best observed in FIG. 2, both follower slots 27M and 27L may not be substantially arcuate, but are shown instead as having a chicane-like disruption, for example segmenting each of the follower slots 27M and 27L into a pair of arcuate portions. These offsetting chicane-like disruptions are placed relative to one another to assist in creating the corrective constraint 30 shown in FIG. 5. For example, the chicane-like disruptions can ensure the concurrent movement of the followers 26M and 26L in the follower slots 27M and 27L, respectively, by increasing the friction during the follower movement. In the knee brace 10, the shape of the follower slots 27M and 27L may be the main driver in the corrective constraints imposed by the knee brace 10. Moreover, the length of the follower slots 27M and 27L may be such as to define end of movements for the followers 26M and 26L, and hence provide a safety against over extension or over flexion of the knee. It is therefore contemplated to machine the follower slots 27M and 27L in a customer-unique fashion, based on the diagnosed corrective movements. In an embodiment, all parts of the knee brace 10 are stock, but for the follower slots 27M and 27L. Different manufacturing techniques support the fabrication of customer-unique follower slots 27M and 27L, such as, but not limited to, laser cutting, additive printing, numerical control machining.

According to an embodiment, the plates 28 are fabricated pursuant to a dynamic analysis of the leg movement of the patient. Kinematic movement analyses are commonly performed to obtain accurate quantitative data representing the movement of the shank S relative to the tight T. It is therefore possible to diagnose corrective movements required based on the quantitative data. Accordingly, a patient corrective movement may be obtained, for instance in the form of distance values for 30M and 30L (FIG. 4).

Figure 7:
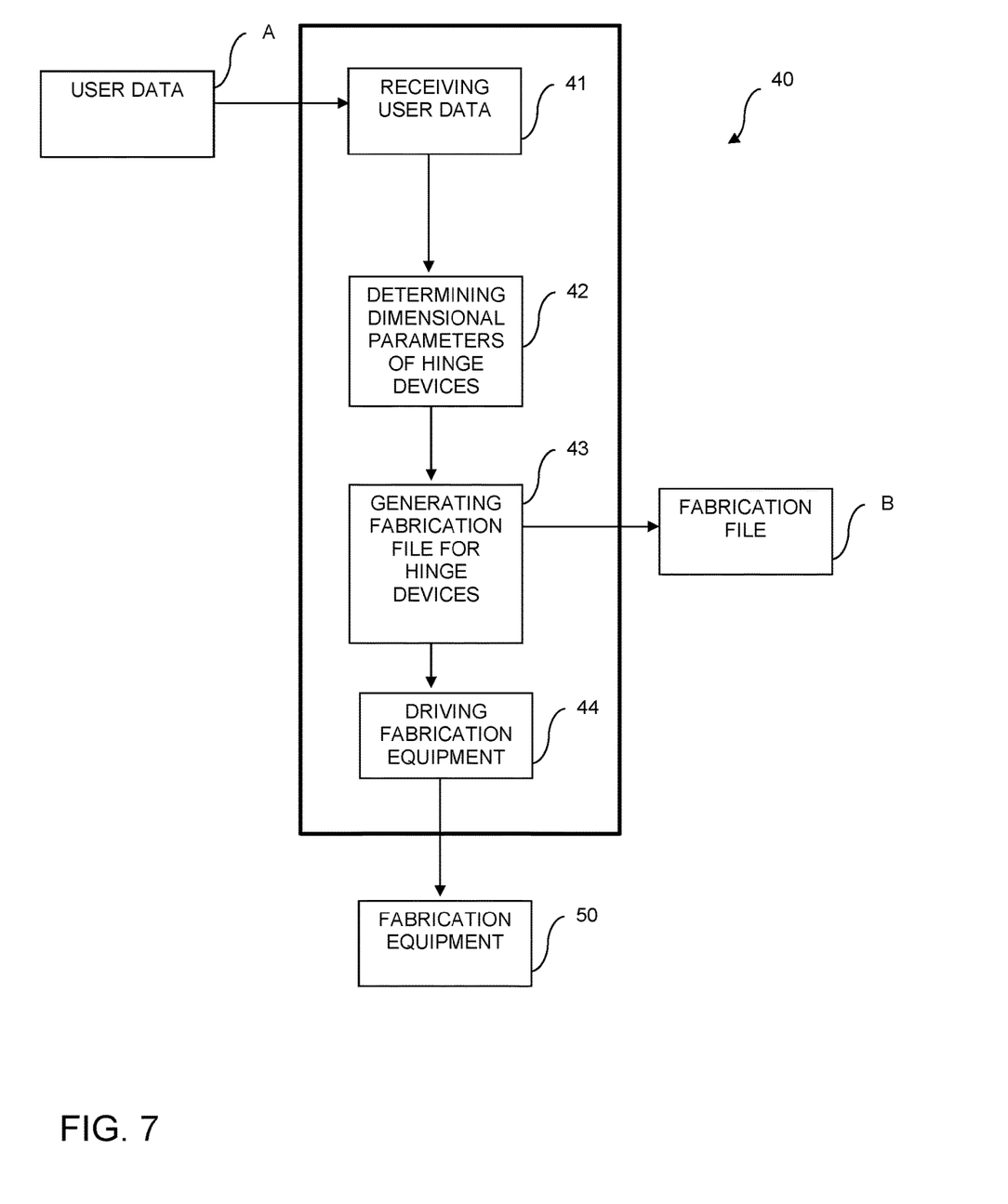
FIG. 7 is a block diagram of a system for generating and manufacturing a knee brace customized to a patient.

Referring to FIG. 7, there is illustrated steps performed by a system 40 to generate and manufacture a knee brace or components thereof customized to a patient, such as the knee brace 10. The system 40 is of the type having a processing unit that has suitable computing speed for the steps described below. The system 40 may also include a non-transitory computer-readable memory communicatively coupled to the processing unit and comprising computer-readable program instructions executable by the processing unit for performing various steps, or operating various modules.

In accordance with 41, the system 40 receives user data related to the knee brace (e.g., the knee brace 10). The user data may be a digital user data file A, that may come from various sources: Dynamic analysis, kinematic movement analysis, data entry from medical personnel, such as orthotist, physicians, surgeons, orthopedists, physiotherapists, etc. The user data may include a desired lengthening value for the leg in extension, to cause the movement displayed in FIG. 3 as 30M, specific to the patient, and for instance as determined by applicable sources. The user data may include a desired rotation value for the leg in extension, to cause the movement as displayed in FIG. 4 as 30L. The user data may also include medial displacement of the knee brace pivot axis X, such as 30M, a concurrent lateral displacement of the knee brace pivot axis X, such as 30L, through flexion and extension. The patient lengthening value and the patient rotation value are indicative of a corrective constraint to leg movement specific to the patient. The user data may also include spacing between width of the knee joint J along the axis X, patient height, shank and thigh diameters for the cuffs or like limb attachment, flexion and extension angles.

In accordance with 42, the system 40 determines dimensional parameters of the the medial hinge device 20M and of a lateral hinge device 20L as a function of the user data. More particularly, the system 40 may use the lengthening value and the rotation value of 41. If available, the system 40 may use the medial displacement 30M of the knee brace pivot axis X and the concurrent lateral displacement 30L of the knee brace pivot axis X, to determine the dimensional parameters. The size of the pivot slots 26 may also be determined. The medial and lateral points for the pivot axis X, and the anticipated space between the hinge devices 20M and 20L along the axis X, may also be used, for instance as a function of the knee width. Dimensional parameters may include one or more of the size and shape of the follower slots 27, the position and orientation of the medial and lateral follower slots 27 relative to one another, the relative position and orientation and/or sizing of all components of the assemblies including any correlation between pivots 24, pivot slots 25, followers 26 and follower slots 27. According to an embodiment, the system 40 determines the dimensional parameters by simulating movements of three dimension models of the hinge devices 20 with various positions, orientations and sizes, to achieve the desired lengthening value and the desired rotation value, as a function of other parameters as mentioned above.

In 43, the system 40 generates a fabrication file for fabricating components of the medial hinge device and of the lateral hinge device having follower slots with the determined dimensional parameters. The format of the fabrication file may be dependent on the fabricating technique. Examples of fabricating techniques include NC machining, rapid prototyping, additive printing, laser cutting, casting, stereolithography, among possibilities. In an embodiment, only the plates 28 are custom fabricated, while other components are stock. Accordingly, the fabrication file may include data related to the other components, such as component identity (e.g., part number), part size, etc. The system 40 may output the fabrication file as B for third party use.

In 22, the system 40 drives fabrication equipment 50 in fabricating the custom fabricated components of the knee brace, such as the plates 28. For example, the system 40 may be integrated or connected to a processor of the fabrication equipment 50, such that the fabrication equipment 50 fabricates the custom fabricated components of the knee brace 10 in accordance with the fabrication file B.

The above description is meant to be exemplary only, and one skilled in the art will recognize that changes may be made to the embodiments described without departing from the scope of the invention disclosed. For example, the knee brace 10 may have additional custom parts, the knee brace 10 may come in various generic sizes with quantified corrective constraint values, etc. According to another embodiment, while the plates 28 and complementary arm end fitted between the plates are shown as being flat, these components may be spherical segments, to form spherical joint surfaces for movement of the complementary arm ends between the plates 28. Although customizing has been described, it is contemplated to fabricate stock knee braces 10 with given corrective constraints. Also, in spite of the description of medial upward movement and lateral rearward movement, other movement directions may be performed. Still other modifications which fall within the scope of the present invention will be apparent to those skilled in the art, in light of a review of this disclosure, and such modifications are intended to fall within the appended claims.

The invention claimed is:

1. A system for generating a knee brace customized to a patient, comprising:
   a processing unit; and
   a non-transitory computer-readable memory communicatively coupled to the processing unit and comprising computer-readable program instructions executable by the processing unit for:
      receiving user data including at least a lengthening value and a rotation value for the knee joint of the user, the user data being indicative of a corrective constraint to leg movement specific to the user;
      determining dimensional parameters of a medial hinge device and of a lateral hinge device as a function of the user data by determining a size and a shape of follower slots in each of the medial hinge device and of the lateral hinge device; and
      generating a fabrication file for fabricating components of the medial hinge device and of the lateral hinge device with the determined dimensional parameters.

2. The system according to claim 1, further comprising outputting the fabrication file.

3. The system according to claim 1, further comprising fabricating the components of the medial hinge device and of the lateral hinge device using the fabrication file.

4. The system according to claim 3, wherein fabricating the components comprises driving fabrication equipment to fabricate the components.

5. The system according to claim 1, further including determining a position and orientation of the follower slots relative to one another.

6. The system according to claim 1, wherein determining the dimensional parameters includes determining a position and orientation of set of pivot and pivot slot in both the medial hinge device and lateral hinge device.

7. The system according to claim 1, wherein determining the dimensional parameters includes simulating movement of a virtual model of a knee brace to obtain the lengthening value and a rotation value.

8. A system for generating a knee brace customized to a patient, comprising:
- a processing unit; and
- a non-transitory computer-readable memory communicatively coupled to the processing unit and comprising computer-readable program instructions executable by the processing unit for:
  - receiving user data including at least a lengthening value and a rotation value for the knee joint of the user, the user data being indicative of a corrective constraint to leg movement specific to the user;
  - determining dimensional parameters of a medial hinge device and of a lateral hinge device as a function of the user data by determining a position and orientation of set of pivot and pivot slot in both the medial hinge device and lateral hinge device; and
  - generating a fabrication file for fabricating components of the medial hinge device and of the lateral hinge device with the determined dimensional parameters.

9. The system according to claim 8, further comprising outputting the fabrication file.

10. The system according to claim 8, further comprising fabricating the components of the medial hinge device and of the lateral hinge device using the fabrication file.

11. The system according to claim 10, wherein fabricating the components comprises driving fabrication equipment to fabricate the components.

12. The system according to claim 8, wherein determining the dimensional parameters includes determining a size and a shape of follower slots in each of the medial hinge device and of the lateral hinge device and determining a position and orientation of the follower slots relative to one another.

13. The system according to claim 8, wherein determining the dimensional parameters includes simulating movement of a virtual model of a knee brace to obtain the lengthening value and a rotation value.

14. A system for generating a knee brace customized to a patient, comprising:
- a processing unit; and
- a non-transitory computer-readable memory communicatively coupled to the processing unit and comprising computer-readable program instructions executable by the processing unit for:
  - receiving user data including at least a lengthening value and a rotation value for the knee joint of the user, the user data being indicative of a corrective constraint to leg movement specific to the user;
  - determining dimensional parameters of a medial hinge device and of a lateral hinge device as a function of the user data by determining the dimensional parameters includes simulating movement of a virtual model of a knee brace to obtain the lengthening value and a rotation value; and
  - generating a fabrication file for fabricating components of the medial hinge device and of the lateral hinge device with the determined dimensional parameters.

15. The system according to claim 14, further comprising outputting the fabrication file.

16. The system according to claim 14, further comprising fabricating the components of the medial hinge device and of the lateral hinge device using the fabrication file.

17. The system according to claim 16, wherein fabricating the components comprises driving fabrication equipment to fabricate the components.

18. The system according to claim 14, wherein determining the dimensional parameters includes determining a size and a shape of follower slots in each of the medial hinge device and of the lateral hinge device and determining a position and orientation of the follower slots relative to one another.

* * * * *